United States Patent
Koshti et al.

(10) Patent No.: US 7,087,692 B2
(45) Date of Patent: Aug. 8, 2006

(54) SALT AND HEAT SENSITIVE, SUBSTANTIVE UV-ABSORBING POLYMERS

(75) Inventors: Nimul Madhukar Koshti, Mumbai (IN); Shubhangi Dattaram Naik, Thane (IN)

(73) Assignee: Galaxy Surfactants LTD, Mumbai (IN)

( * ) Notice: Subject to any disclaimer, the term of this patent is extended or adjusted under 35 U.S.C. 154(b) by 570 days.

(21) Appl. No.: 10/305,087

(22) Filed: Nov. 27, 2002

(65) Prior Publication Data

US 2004/0101498 A1    May 27, 2004

(51) Int. Cl.
*C08F 112/08*    (2006.01)
(52) U.S. Cl. .................... 526/217; 526/347.1
(58) Field of Classification Search ............... 526/217, 526/347.1
See application file for complete search history.

(56) References Cited

U.S. PATENT DOCUMENTS 4,704,324 A * 11/1987 Davis et al. ............. 428/308.4

* cited by examiner

*Primary Examiner*—Robert D. Harlan
(74) *Attorney, Agent, or Firm*—Westerman, Hattori, Daniels & Adrian, LLP.

(57) ABSTRACT

Substantive UV-absorbing, water-soluble, cationic polymers containing cinnamidoalkylamines and benzamidoalkylamines, with 'inverse temperature dependant solubility' are described in the present invention. They are water-soluble at ambient conditions and yet they are water-resistant at the temperature of human body as well as in the presence of electrolytes. These properties make these macromolecules useful for personal care as well as fabric care products.

The present invention also describes the hair, skin and fabric care compositions containing the said polymers of Formula I wherein, ArCO is an UV-absorbing moiety of an organic sunscreen acid or mixtures of organic sunscreen acids selected from p-methoxy cinnamic acid and p-dimethyl amino benzoic acid; $R_2$ and $R_3$ are selected from hydrogen, alkyl and cycloalkyl group containing from 1 to 6 carbon atoms; m is an integer from 5 to 9 and n is an integer between 1 to 5 and m+n=10

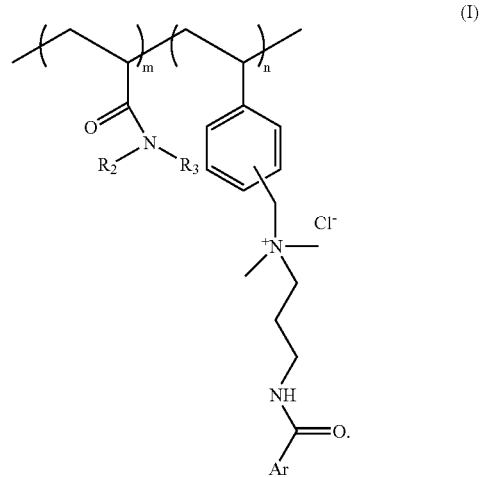

2 Claims, No Drawings

SALT AND HEAT SENSITIVE, SUBSTANTIVE UV-ABSORBING POLYMERS

FIELD OF INVENTION

This invention relates to substantive, water-soluble, cationic, salt and heat sensitive, UV-absorbing polymers. More particularly, this invention relates to novel, non-hydrolysable, non-irritating, UV-absorbing polymers containing cinnamidoalkylamine and/or benzamidoalkylamine moieties that are substantive to skin, hair and fabric. This invention also relates to a process of manufacture of the said polymers and further to their use in skin, hair and fabric care formulations.

BACKGROUND AND PRIOR ART

U.S. Pat. No. 3,864,473 (1975) reveals substantive sunscreen polymer based on polyethyleneimine and p-N,N-dimethylaminobenzoic acid. U.S. Pat. No. 4,004,074 (1977) provides substantive polymeric sunscreen agents comprising an UV-absorbing moiety selected from salicylates, aminobenzoates and carboxy succinates and a substrate linking moiety selected from the group consisting of thiocarboxylic acids, mercaptans, guanidines and biguanidines. U.S. Pat. No. 4,233,430 (1980) discloses an antisolar acrylamide backbone polymer containing coumarins, benzothiazoles, 3-(acrylamidomethylbenzylidine) DL camphor as sunscreen moieties. The water insoluble polymers of this invention are used in leave-on applications like antisolar lotion, cream, aerosol and oil. U.S. Pat. No. 4,524,061 (1985) teaches the art of making polymeric sunscreen agents that comprise of olefinic p-aminobenzoate, N-vinylpyrrolidinone, a vinyl lactam and acrylic or methacrylic acid. The polymeric sunscreens are claimed to have good adhesion to skin and to resist removal by salt or plain water. They are claimed to form a thin film that is easily removable by mildly alkaline soap or shampoo.

Interestingly, U.S. Pat. No. 5,204,090 (1993) discloses use of combination of water insoluble film forming acrylic polymer and sunscreen agents to yield water proof high SPF compositions. U.S. Pat. No. 4,508,882 (1985) employs UV-absorbing benzotriazole having vinyl group to make homopolymers as well as copolymers that are most effectively used for UV protection of plastics and wood. U.S. Pat. No. 5,063,048 (1991) discloses UV light absorbing skin-protecting composition based on acrylic polymeric backbone containing salicylates, benzophenones and benzotriazoles as sunscreen moieties.

It is pertinent to mention here that all the polymeric sunscreens reported so far have been water-insoluble. It was in 1992–93, U.S. Pat. No. 5,134,223 (1992), U.S. Pat. No. 5,243,021 (1993), U.S. Pat. No. 5,250,652 (1993) disclosed novel, water dispersible copolymers that contain UV-absorbing monomers based on moieties such as aminobenzoates and hydrophilicity was introduced by polyethylene glycol backbone.

Polymer bound 2-(2-hydroxyphenyl)2H-benzotriazole as UV absorber is disclosed by U.S. Pat. No. 5,099,027 (1992) for any exterior coating application (as in manufacture of optical lenses) and as components for sunscreening and suntanning lotions.

On the similar lines U.S. Pat. No. 5,487,885 (1996) and U.S. Pat. No. 5,741,924 (1998) provide acrylic polymers with UV absorbing moieties having different ranges in conjugation with another hydrophilic monomer. The polymers are insoluble in water but reported to swell in water and are meant for dermatological formulation that can be coated, sprayed, spread on the surface and are claimed not to unduly penetrate the dermal layer. Use of such polymers in coating of lens surface and in other opthalmological solutions is described. The UV absorbing moieties cover derivatives of dibenzoyl methanes, dimethylamino benzoates and phenyl benzamides.

From above discussion it is clear that a polymeric sunscreens of prior art are substantive by virtue of their film forming nature. Only exception is U.S. Pat. No. 4,004,074 (1977) where substantivity to skin was achieved through substrate linking groups like thiocarboxylic acids and mercaptans, etc.

Most of the UV-absorbing polymers reported so far are water-insoluble. To make these polymers useful for personal care products they need to be formulated with hydrophobic bases that give greasy feel. The water-insoluble polymers can be applied by aerosol spray preparations. However, the water-resistant films they form are quite difficult to remove. Hence there is a need to synthesise polymeric sunscreens that are water-soluble yet water-resistant once they are applied to skin, hair or fabric.

This is achieved in the present invention by synthesising water-soluble polymers containing cinnamidoalkylamines and/or benzamidoalkylamines that (a) have lower critical solution temperature (LCST) of 30° C. or above and (b) cationic centres for enhanced substantivity. When these water-soluble polymers are applied to skin, the temperature of body as well as the temperature of surroundling and the salt content of water (in case of swimming in the sea) make them insoluble and hence do not get easily washed off either by sweat or sea water. However, they can be easily removed by plain water (without salt) at ambient temperature (25° C.). These UV-absorbing polymers show excellent substantivity to hair as a result of cationic centres.

The main object of the present invention is to synthesise water-soluble macromolecules with cinnamido and benzamido moieties to provide UV-absorption and to provide significant levels of substantivity especially during an activity like swimming. Another object of the present invention is to prepare useful cosmetic formulations and formulations for fabric care employing these new UV-absorbing macromolecules.

SUMMARY OF THE INVENTION

The present invention provides water-soluble, cationic, salt and heat sensitive, UV-absorbing polymers as represented by Formula I;

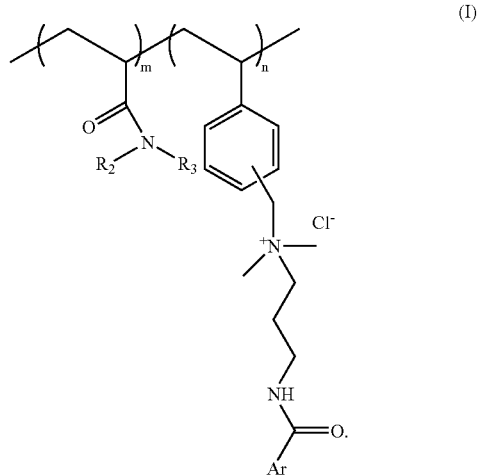

wherein ArCO is an UV-absorbing moiety of an organic sunscreen acid or mixtures of organic sunscreen acids selected from p-methoxy cinnamic acid and p-dimethyl amino benzoic acid;

$R_2$ and $R_3$ are selected from hydrogen, alkyl and cycloalkyl group containing from 1 to 6 carbon atoms;

m is an integer from 5 to 9 and n is an integer between 1 to 5 and m+n=10.

A preferred polymer of Formula I is the one wherein, ArCO=p-methoxy cinnamoyl, $R_2$=—H, $R_3$=isopropyl; mole ratio, m:n::8:2.

In another aspect, the invention relates to a process of making polymers of Formula I,

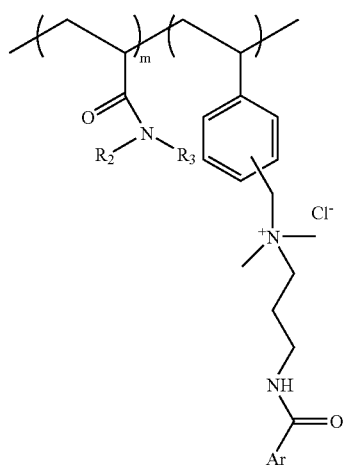
(I)

wherein ArCO is an UV-absorbing moiety of an organic sunscreen acid or mixtures of organic sunscreen acids selected from p-methoxy cinnamic acid and p-dimethyl amino benzoic acid;

$R_2$ and $R_3$ are selected from hydrogen, alkyl and cycloalkyl group containing from 1 to 6 carbon atoms;

m is an integer from 5 to 9 and n is an integer between 1 to 5 and m+n=10;

wherein a compound of Formula II is reacted with N,N-dimethyl propyl diamine to give an intermediate of Formula III that is quaternised with compound of Formula V, a copolymer of compound of Formula IV and vinyl benzyl chloride, wherein Ar, $R_2$, $R_3$, m and n are the same as in Formula I and $R_1$ is —OH, —Cl or —O(CH$_2$)$_p$CH$_3$ (p=0 to 3).

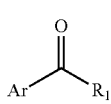
(II)

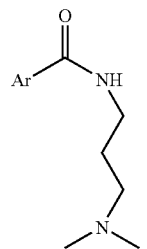
(III)

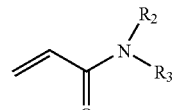
(IV)

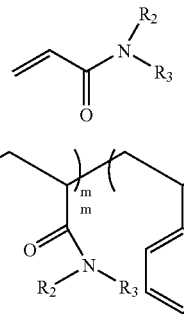
(V)

In another aspect, this invention provides compositions containing the said UV-absorbing polymers for hair, skin and fabric care.

DETAILED DESCRIPTION OF THE INVENTION

The synthesis of the polymers represented by Formula I is carried out in three steps, (a) synthesis of cinnamidoalkylamines and/or benzainidoalkylamines, (b) copolymerisation of monomer of Formula IV and vinyl benzyl chloride, (c) functionalisation of this copolymer by quaternisation. (a) Synthesis of cinnamidoalkylamines and/or benzamidoalkylamines:

In this process, the synthesis of cinnamidoalkylamines and/or benzamidoalkylamines involves, the amidification reaction between a compound of the Formula II when $R_1$=—OH or O—(CH$_2$)$_p$CH$_3$ (p=0 to 3), with N,N-dimethyl propyl diamine. It is carried in one embodiment of the invention, under pressure from about 10 psi to about 100 psi, in the presence of a basic catalyst such as sodium methoxide, sodium hydroxide from 0.25% to 5.0% by weight of the reaction mass at from about 120° C. to about 200° C., to afford the intermediate compound of Formula III. The preferred amount of such a catalyst is 1.0% w/w. The reaction is conveniently monitored by TLC using Merck's silica gel coated on either aluminium of plastic or reversed phase HPLC using UV detection. After the complete disappearance of Formula II, the excess diamine is distilled off under vacuum.

The compounds of Formula III are synthesised by reacting acid chlorides of Formula II (1.0 mole) when $R_1$ is —Cl with the N,N-dimethyl propyl diamine (1.0 to 1.2 mole) at 20–50° C. in an inert solvent like dichloromethane, ethylene dichloride, tetrahydrofuran and the like. The amidification reaction between a compound of Formula II when $R_1$=—Cl is carried out with N,N-dimethyl propyl diamine at room temperature in the presence of a solvent.

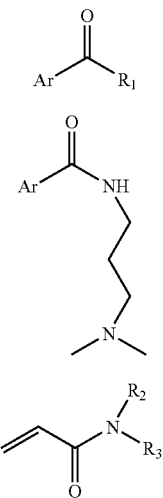

(II)

(III)

(IV)

(b) copolymerisation of monomer of Formula IV and vinyl benzyl chloride:

Copolymerisation of monomers of Formula IV and vinyl benzyl chloride (single isomer or mixture of isomers) is carried out in an inert atmosphere of either nitrogen or argon at temperature from about 60 to 120° C., in a suitable solvent in the presence of an initiator.

The concentration of monomers, substituted alkylacrylamides (Formula IV) and vinyl benzyl chloride in reaction mixture ranges from 10% to 50%, preferably 20 to 30% by weight of reaction mass, the balance being the solvent. The mole ratio of compounds of Formula IV to vinyl benzyl chloride varies from 5:5::9:1. The preferred mole ratio of the two monomers is 8:2. The polymerisation is carried out in protic solvents such as lower alcohols (containing carbons from 1 to 4) or glycols, aprotic polar solvents like DMF and DMSO and combinations thereof.

The peroxy or azo initiators in polyinerisation step of this process are employed from about 0.1 % to 5.0% by weight of total mass of monomers. A variety of organic as well as inorganic peroxy initiators are used such as dibenzoyl peroxide, dilauroyl peroxide, ammonium persulphate and the like. Similarly, amongst a variety of azo initiators such as azocyanovaleric acid, azobisisobytyronitrile, azobiscyclohexanecarbonitrile and the like can be employed. Thus, the temperature for polymerisation is dictated by (a) monomer concentration, (b) the catalyst and (c) the solvent. The preferred conditions for polymerisations are such that the copolymer that is formed has average molecular weight of around $5 \times 10^5$.

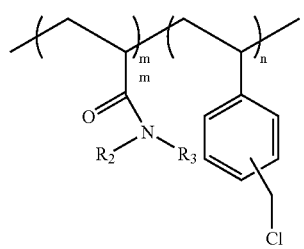

(V)

(c) functionalisation of copolymer by quaternisation:

The quaternisation of cinnamidoalkylamine and/or benzamidoalkylamine (Formula III) is carried out with copolymer of substituted alkylacrylamides and vinyl benzyl chloride in the presence of a suitable solvent such as DMF, lower alcohols and glycols having carbon atoms from 1 to 6 or aqueous solution of these solvents. The temperature of quaternisation ranges from 60 to 120° C. and the duration ranges from about 8 to 16 hours depending upon the solvent. The completion of reaction is ascertained by estimation of liberated Cl$^-$, the anion of quaternary nitrogen. The quaternisation of the copolymer gives water-soluble cationic macromolecules with UV absorbing cinnamido and/or benzainido moiety (Formula I).

Thus, the copolymer can be functionalised by reacting with cinnamidoalkylamine and/or benzamidoalkylamine (Formula III) to generate cationic polymers (Formula I) with substantivity to skin, hair and fabric. In functionalised polymers of Formula I, mole ratio of m:n varies from 5:5 to 9:1. The preferred ratio for m:n is between 8:2. The copolymers thus obtained are water-soluble with lower critical solution temperature (LCST) of 30° C. or above. This means at or above 30° C. the polymer phase-separates from its aqueous solution. Addition of small quantities of electrolytes also results in lowering of LCST and polymer loses its solubility and precipitates out. This inverse temperature dependant solubility behaviour of aqueous solution of these polymers is also exploited for their purification. The phase-separated polymers can either be dissolved in water or alcoholic solvents for their final use in formulations.

The number and the nature of the substituents selected is such that they do not render the final cationic polymers water-insoluble.

The preferred substituents in cationic polymers of Formula I containing cinnamidoalkylamine and/or benzamidoalkylamine are as follows;

ArCO is an UV-absorbing moiety of an organic sunscreen acid or mixtures of organic sunscreen acids selected from p-methoxy cinnamic acid and p-dimethyl amino benzoic acid. Referring again to Formula I, the groups $R_2$ and $R_3$ are selected from H, alkyl or cycloalkyl groups containing from 1 to 6 carbon atoms.

The cationic polymers of the present invention are formed by quaternising tertiary amines of Formula III by the copolymer made from compounds of Formula IV and vinyl benzyl chloride. The cationic polymers of the present invention, will also include an anion derived from quaternisation reactions. Thus, the cationic polymers of the present invention have Cl$^-$ as the anion.

In another embodiment the process of the present invention relates to manufacture of cationic, UV absorbing, water-soluble polymers of Formula I, shown in the accompanying drawing, in which ArCO is an UV-absorbing moiety of an organic sunscreen acid or mixtures of organic sunscreen acids selected from p-methoxy cinnamic acid and p-dimethyl amino benzoic acid; $R_2$ and $R_3$ are selected from hydrogen, alkyl or cycloalkyl groups containing from 1 to 6 carbon atoms; the mole ratio of m:n is from 5:5 to 9:1, from the compounds of Formula II, III, IV, and V shown in the accompanying drawing, with respective substituents ArCO of Formula II, $R_2$ and $R_3$ of Formula IV as defined for the polymers of Formula I, in this embodiment and $R_1$ of Formula II being —OH, —Cl, —Br or —O(CH$_2$)$_p$CH$_3$(p=0 to 3).

In another embodiment the process of the present invention relates to manufacture of cationic, UV absorbing, water-soluble polymers of Formula I, shown in the accompanying drawing, in which ArCO=p-methoxy cinnamoyl, $R_2$=—H, $R_3$=isopropyl, the mole ratio, m:n is 8:2, from the compounds of Formula II (ethyl p-methoxy cinnamate, ArCO=p-methoxy cinnamoyl and $R_1$=—$OC_2H_5$) and N,N-dimethylpropyldiamine, forming an intermediate compound of Formula III (p-methoxy cinnamidopropyldimethyl amine, ArCO=p-methoxy cinnamoyl), Formula IV (N-isopropyl acrylamide, $R_2$=—H, $R_3$=isopropyl) and Formula V (copolymer, m:n::8:2). Along with the synthesis of this polymeric UV-absorber, its substantivity and photoprotection efficacy to skin are described in Example 1.

In another embodiment the process of the present invention relates to manufacture of cationic, UV absorbing, water-soluble polymers of Formula I, shown in the accompanying drawing, in which ArCO=p-dimethylamino benzoyl, $R_2$=—H, $R_3$=isopropyl, the mole ratio, m:n is 8:2, from the compounds of Formula II (ethyl p-dimethylamino benzoate, ArCO=p-dimethylamino benzoyl and $R_1$=—$OC_2H_5$) and N,N-dimethylpropyldiamine, forming an intermediate compound of Formula III (p-dimethylamino benzamidopropyldimethyl amine, ArCO=p-dimethylamino benzoyl), Formula IV (N-isopropyl acrylamide, $R_2$=—H, $R_3$=isopropyl) and Formula V (copolymer, m:n::8:2). The synthesis of this UV-absorbing polymer is described in Example III.

In another embodiment the process of the present invention relates to manufacture of cationic, UV absorbing, water-soluble polymers of Formula I, shown in the accompanying drawing, in which ArCO=p-methoxy cinnamoyl, $R_2$, $R_3$=—$C_2H_5$, the mole ratio m:n is 8:2, from the compounds of Formula II (p-methoxy cinnainoyl chloride, ArCO=p-methoxy cinnamoyl and $R_1$=—Cl) and N,N-dimethylpropyldiamine, forming an intermediate compound of Formula III (p-methoxy cinnamidopropyldimethyl amine, ArCO=p-methoxy cinnamoyl), Formula IV (N,N-diethyl acrylamide, $R_2$, $R_3$=—$C_2H_5$) and Formula V (copolymer, m:n::8:2). The synthesis of this UV-absorbing polymer is described in Example II.

The UV-absorbing polymers are white solids and are soluble in water and protic solvents and mixtures thereof. A typical 8:2 polymer has $E^{1\%}_{1\ cm}$ of around 200 at 298–300 nm. The polymers precipitate from their aqueous solution when heated above 30° C. Addition of simple electrolytes like sodium chloride induces quantitative precipitation. The photoprotection efficacy and substantivity of this polymer is described in Example I.

Skin Care Compositions

Lotions are formed using polymers of Formula I, with or without one or more of the inert solvents like ethyl alcohol, isopropyl alcohol or propylene glycol, by combining with film forming polymers like proteins, polyvinyl pyrrolidone, polyvinyl alcohols and the like, film-forming starches and resins and the like.

Oil-in-water and water-in-oil emulsion can be made in the form of lotions and creams. Conventional oil soluble UV-absorbing compounds like cinnamates, salicylates, p-aminobenzoates, benzophenones can be dissolved in oily phase of emulsion/lotions. The water-soluble sunscreens of the present invention are dissolved in an aqueous phase of the emulsion and combined with the oily phase using a suitable cationic emulsifier such as stearylkonium chloride or non-ionic emulsifiers such as sorbitan oleate ethoxylate (polysorbate-80) and fatty alcohol ethoxylates. Vegetable or mineral oils suitable for use as oil phase include mineral oil, petroleum jelly, castor oil, sesame oil and the like.

Perfumes, fragrances, essential oils, anti-oxidants, preservatives, dyes, colorants, insect repellents, emollients, humectants, thickeners, other sunscreen agents, surfactants, herbal extracts may be optionally included in the sunscreen and tanning compositions of the present invention.

The sunscreen and tanning compositions of the present invention contain an effective amount of cationic polymer of Formula I to prevent erythema. In general, an amount of about 0.5% to 10% w/w of the total composition is used.

A skin care sunscreen formulation, wherein, cationic polymer of Formula I are in aqueous phase and other oil soluble sunscreen are in oil phase and the said composition is an emulsion.

Skin care compositions of the present invention contain polymers of Formula I from about 0.5% to about 5.0% w/w of total composition with UV-A sunscreens like benzophenones, dibenzoyl methanes, etc. Such preparations also contain skin lightening agents like niacinamide, kojic acid or hydroquinone, for prevention of melanin formation; and herbal extracts like curcuma longa, santalum album.

A skin care formulation can be prepared using polymers of Formula I with substituent, $R_2$, $R_3$=hydrogen, alkyl or cycloalkyl group containing from 1 to 6 carbon atoms and ArCO is an UV-absorbing moiety of an organic sunscreen acid or mixtures of organic sunscreen acids selected from p-methoxy cinnamic acid and p-dimethyl amino benzoic acid and m is an integer from 5 to 9 and n is an integer between 1 to 5 and m+n=10, about 2.0% w/w and other sunscreen formulation ingredients such as water-insoluble sunscreen Galaxy—TosyQuat (CTFA name—p-methoxy cinnamido propyl laurdimonium tosylate), about 1.0% w/w and UV-A sunscreen, Parsol-1789 (methoxy butyl dibenzoyl methane) about 1.0% w/w.

Rinse-off products like face-wash and bathing bars of the present invention contain from about 1.0 to 10.0% w/w of substantive UV-B absorbing polymers of Formula I in combination with other sunscreen molecules that may or may not be substantive.

A skin care transparent bathing bar formulation can be made using polymers of Formula I with substituent, $R_2$, $R_3$=hydrogen, alkyl or cycloalkyl group containing from 1 to 6 carbon atoms and ArCO is an UV-absorbing moiety of an organic sunscreen acid or mixtures of organic sunscreen acids selected from p-methoxy cinnamic acid and p-dimethyl amino benzoic acid and m is an integer from 5 to 9 and n is an integer between 1 to 5 and m+n=10, about 1.0% w/w, and other usual transparent bathing bar ingredients such as SLES-2, about 28.0% w/w; cocoamidopropyl betaine, about 16.0% w/w; propylene glycol, about 20.0% w/w; sorbitol, about 8.0% w/w; sodium cocoate, about 9.0% w/w and sodium stearate, about 13.8% w/w.

Hair Care Compositions

The hair care compositions containing polymers of Formula I may contain one or more ingredients selected form cosmetic agents such as surfactants, other sunscreen chemicals, after sun treatment materials, emollients, humectants, perfumes, moisturisers, color cosmetic materials, herbal extracts, occlusive oils and essential oils.

The compositions contain polymers of Formula I with or without UV-A sunscreen agents to protect hair from UV radiation. By virtue of being cationics, they also provide good conditioning effect. The hair protecting preparations can be formulated in the form of creams, lotions, tonics, gels, hair dressings—pomades, brilliantines, hair oils, shampoos, cream rinses, hair conditioners, hair relaxers, hair coloring products and the like.

The rinse-off preparations like shampoos contain 0.5 to 8.0% w/w of compounds of Formula I. It may be noted that these polymers of Formula I are compatible with usual anti-dandruff agents like Zinc pyrithione, Pyroctone and hence can be incorporated in anti-dandruff shampoos.

A hair care shampoo formulation can be made using polymers of Formula I with substituent, $R_2$, $R_3$=hydrogen, alkyl or cycloalkyl group containing from 1 to 6 carbon atoms and ArCO is an UV-absorbing moiety of an organic sunscreen acid or mixtures of organic sunscreen acids selected from p-methoxy cinnamic acid and p-dimethyl amino benzoic acid and m is an integer from 5 to 9 and n is an integer between 1 to 5 and m+n=10, about 1.0% w/w and other usual shampoo ingredients such as SLES-2, about 50% w/w; cocoamidopropylbetaine, about 2.5% w/w; lauryl amine oxide, about 2.0% w/w.

A hair care transparent gel formulation can be made using polymers of Formula I with substituent, $R_2$, $R_3$=hydrogen, alkyl or cycloalkyl group containing from 1 to 6 carbon atoms and ArCO is an UV-absorbing moiety of an organic sunscreen acid or mixtures of organic sunscreen acids selected from p-methoxy cinnamic acid and p-dimethyl amino benzoic acid and m is an integer from 5 to 9 and n is an integer between 1 to 5 and m+n=10, about 0.5% w/w and other usual gel ingredients such as Carbopol—Ultrez-10, about 1.0% w/w.

A sunscreen spray formulation for both hair and skin can be made using polymers of Formula I with substituent, $R_2$, $R_3$=hydrogen, alkyl or cycloalkyl group containing from 1 to 6 carbon atoms and ArCO is an UV-absorbing moiety of an organic sunscreen acid or mixtures of organic sunscreen acids selected from p-methoxy cinnamic acid and p-dimethyl amino benzoic acid and m is an integer from 5 to 9 and n is an integer between 1 to 5 and m+n=10, about 8.0% w/w and silicone copolyol, about 2.0% w/w.

Fabric Care Compositions

Fabric care compositions such as detergent powder or liquid detergent can contain 1.0 to 10.0% w/w of polymers of Formula I. These fabric substantive UV absorbers can also be incorporated in after-wash formulations to protect coloured garments from fading due to exposure to sunlight.

A fabric care detergent powder formulation can be made using polymers of Formula I with substituents, $R_2$, $R_3$=hydrogen, alkyl or cycloalkyl group containing from 1 to 6 carbon atoms and ArCO is an UV-absorbing moiety of an organic sunscreen acid or mixtures of organic sunscreen acids selected from p-methoxy cinnamic acid and p-dimethyl amino benzoic acid m is an integer from 5 to 9 and n is an integer between 1 to 5 and m+n=10, about 2.0% w/w and other detergent powder ingredients such as soda ash, about 20.0% w/w; sodium tripolyphosphate, about 25.0% w/w and sodium linear alkyl benzene sulphonate, about 20.0% w/w.

After wash fabric softener can be made using biodegradable triethanolamine esterquat, 5.0% w/w and 0.5% w/w of polymers of the present invention.

In general, an amount of about 0.5% to about 10% w/w of total cosmetic composition of polymers of Formula I are useful in hair, skin and fabric care products. Typically, the ingredients are combined with mixing and heating if necessary until a uniform, homogeneous product is formed. With respect to the emulsion products of the present invention, the water-soluble and water-insoluble ingredients are mixed separately and combined with a suitable emulsifier, to form an emulsion.

EXAMPLES

The invention will now be illustrated with the help of examples, Examples I to III for process of manufacture of compounds of Formula I and Examples IV to IX for compositions. The examples are by way of illustrations only and in no way restrict the scope of invention. Many changes and modifications can be made within the scope of the present invention without departing from the spirit thereof and the invention includes all such modifications. Formulae for the preparation of shampoo, transparent bathing bar, sunscreen cream, sunscreen gel, sunscreen spray and detergent powder with compounds of Formula I are illustrated in Examples IV, V, VI, VII, VIII and IX respectively.

Example I p-Methoxy cinnamic acid was obtained from Galaxy Surfactants Ltd., Mumbai, p-dimethylamino benzoic acid was purchased from Nagase Chemical Co., Japan, N,N-dimethyl propyl diamine from BASF, N-isopropyl acrylamide, vinyl benzyl chloride from Seimi, Japan. DMF, t-butanol, methylene chloride, thionyl chloride, acrylic acid and acetone were purchased from S. D. Fine Chem, Mumbai.

Process for Preparation of Cationic Polymer of Formula I; wherein ArCO=p-methoxy cinnamoyl $R_2$=—H, $R_3$=Isopropyl: Mole Ratio, m:n::8:2:

This polymer was synthesised by following three steps;

(a) Preparation of p-methoxy cinnamidopropyldimethylamine:

Ethyl p-methoxy cinnamate (206.0 g, 1.0 mole), N,N-dimethylpropyldiamine (306.0 g, 3.0 mole) and sodium methoxide (2.0 g) were charged in a pressure reactor. The air inside the reactor was flushed out by purging of nitrogen. The reaction mixture was then stirred at 180° C. (this generated pressure of 18 kg/cm$^2$) for 36 hours when p-methoxy cinnamidoalkylamine is formed. The progress of reaction was monitored by disappearance of ethyl p-methoxy cinnamate on chromatography (TLC and HPLC). The TLC was performed on aluminium coated silica gel plates (Merck—60-F-254) and viewed with a UV lamp at 254 nm. HPLC was performed using reversed phase technique on a C-18 bonded (octadecyl silane) column and 60% v/v aqueous methanol as mobile phase (1.0 ml/min) and detection at 280 nm. The excess amine was removed under vacuum. The golden yellow solid (263.0 g) thus obtained had amine value of 220. Molar extinction coefficient, ∈, in methanol was found to be 24,224 at 290 nm. IR in dichloromethane showed carbonyl stretching of amide at 1660 cm$^{-1}$ and NH stretching at 3300 cm$^{-1}$.

$^1$H NMR (300 MHz, CDCl$_3$): δ 1.73 (p, 2H, J=6.6 Hz), 2.26 (s, 6H), 2.42 (t, 2H, J=6.6 Hz), 3.45 (q, 2H, J=6.0 Hz), 3.81 (s, 3H), 6.27 (d, 1H, J=15.6 Hz), 6.86 (d, 2H, J=8.7 Hz), 7.43 (d, 2H, J=8.7 Hz), 7.53 (d, 1H, J=15.6 Hz).

(b) Copolymerisation of N-isopropyl acrylamide and vinyl benzyl chloride (m:n::8:2):

A solution of N-isopropyl acrylamide (10.0 g, 88.8 mmol), vinyl benzyl chloride (3.37 g, 22.1 mmol) and AIBN (100 mg) in t-butanol (120 ml) was stirred under nitrogen blanket at 80° C. for 12 hours. The polymer solution was concentrated to half of its volume using rotary evaporator under vacuum. The copolymer was precipitated by adding concentrated t-butanolic solution to stirred petroleum ether (1000 ml). The precipitated polymer was filtered and dried under high vacuum to yield 12.75 g (95%) of white powder. Mv of the copolymer was found to be around 5×10⁵ (Ubbelohde viscometer).

IR (KBr):1643 cm⁻¹(carbonyl of amide), 3278 cm⁻¹(—NH of amide). ¹H NMR (CDCl₃, 300 MHz): δ (broad signals at 0.89 to 1.6, 2.1, 4.45, 6.4–7.2). Showed total absence of signals due to vinylic protons of monomers.

(c) Quaternisation of p-methoxy cinnamidopropyidimethylamine with poly(N-isopropyl acrylamide-c-vinyl benzyl chloride):

A mixture of copolymer of N-isopropyl acrylamide and vinyl benzyl chloride (3.68 g, 6.1 mmol of vinyl benzyl chloride) from the previous step (b), p-methoxy cinnamidopropyidimethylamine (1.6 g, 6.1 mmol) in isopropanol (50 ml) was stirred under nitrogen at 80° C. for 48 hours. The progress of reaction was followed by estimation of chloride ions. After quantitative liberation of chloride ions (0.38%), the solvent from the reaction mass was removed using a rotary evaporator to give pale yellow coloured powdery solid. This powder was further used for recording IR and NMR. $E^{1\%}_{1\ cm}$ of this quaternised copolymer was found to be 213 at λmax 296 nm in water.

IR (KBr): 1650 cm⁻¹, 3250 cm⁻¹(broad). ¹H NMR (D₂O, 300 MHz): δ (broad signals at 1.05, 2.0–2.1, 2.9–3.1, 3.65–3.85, 6.4–7.6). After quaternisation there is significant increase in aromatic protons relative to aliphatic protons.

1.0% aqueous solution of this polymer had LCST of 35° C. The polymer precipitated quantitatively from its aqueous solution when added to 2.0% sodium chloride solution.

Substantivity and Photoprotection Efficacy:

Aqueous solution (100 mg) containing 10 mg of polymer was applied to a marked area (15 cm²) of forearm and the subject swam in the sea water for 30 minutes in midnoon. The melanin content of the protected skin and the unprotected skin of the forearm was measured. The melanin content of protected skin changed from 334 to 338 units on the Mexameter* after the 30 minutes of swimming in the sea whereas the melanin content of the unprotected skin shot from 334 to 380 units on the Mexameter. After the 30 minutes of swimming, the applied polymer (10 mg) was extracted using cotton swabs soaked in ethyl alcohol. On analysing ethyl alcohol extracts spectrophotometrically, the substantivity to skin was found to be 200 μg/cm².

* Photoprotection efficacy of the polymer of the present invention was estimated by measuring the melanin content by Mexaineter-18. This device is manufactured by Courage-Khazaka Electronic Gmbh, Koln, Germany.

Skin, hair and fabric care formulations were made using this polymer (10% aqueous solution) and its substantivity was determined.

Example II

Process for Preparation of Cationic Polymer of Formula I; wherein ArCO=p-methoxy cinnamoyl, R₂, R₃=—C₂H₅; Mole Ratio, m:n=8:2:

This polymer was synthesised by following four steps;

(a) Preparation of p-methoxy cinnamidopropyldimethylainine:

To a stirred solution of N,N-dimethylpropyldiamine (102.0 g, 1.0 mole) in dichloromethane (500 ml), solution of p-methoxy cinnamoyl chloride (196.0 g, 1.0 mole) in dichloromethane from step (a) was slowly added and the reaction was continued at room temperature for 2 hours. The reaction mixture in dichloroinethane was washed with aqueous sodium hydroxide (200 ml, 20.0%). The organic layer was dried over anhydrous sodium sulphate. The removal of solvent using a rotary evaporator afforded the p-methoxy cinnamidopropyldimethylamine (235.0 g) as colourless solid, m.p. 80° C. Reversed phase HPLC showed it to be 98% pure with amine value 217.

The NMR, IR and HPLC data of p-methoxy cinnamidopropyldimethylamine matched with the data for the compound obtained in Example I.

(b) Copolymerisation of N,N-diethyl acrylamide and vinyl benzyl chloride (m:n::8:2):

A solution of N,N-diethyl acrylamide (10.0 g, 78.74 mmol), vinyl benzyl chloride (3.0 g, 19.67 mmol) and AIBN (100 mg) in t-butanol (120 ml) was stirred under nitrogen blanket at 80° C. for 12 hours. The polymer solution was concentrated to half of its volume using rotary evaporator under vacuum. The copolymer was precipitated by adding concentrated t-butanolic solution to stirred petroleum ether (1000 ml). The precipitated polymer was filtered and dried under high vacuum to yield 12.5 g (96%) of white powder.

(c) Quaternisation of p-methoxy cinnainidopropyldimethylamine with poly(N,N-diethyl acrylamide-c-vinyl benzyl chloride):

A mixture of copolymer of N,N-diethyl acrylainide and vinyl benzyl chloride (3.0 g, 4.54 mmol of vinyl benzyl chloride) from the previous step (b), p-methoxy cinnamidopropyl dimethylamine (1.19 g, 4.54 mmol) in isopropanol (40 ml) was stirred under nitrogen at 80° C. for 48 hours. The progress of reaction was followed by estimation of chloride ions. After quantitative liberation of chloride ions (0.35%), the solvent from the reaction mass was removed using a rotary evaporator to give pale yellow coloured powdery solid. This powder was further used for recording IR and NMR. It was redissolved in water or propylene glycol to form 10% solution. $E^{1\%}_{1\ cm}$ of this quaternised copolymer was found to be 200 at λmax 295 nm.

Example III

Process for Preparation of Cationic Polymer of Formula I: wherein ArCO=p-dimethylamino benzoyl, R₂=—H, R₃=isopropyl; Mole Ratio, m:n=8:2:

This polymer was synthesised by following three steps;

(a) Preparation of p-dimethylamino benzainidopropyldimethylamine:

It was prepared as per the literature procedure described in U.S. Pat. No. 5,427,773 (1995).

(b) Copolymerisation of N-isopropyl acrylainide and vinyl benzyl chloride (m:n::8:2):

As described in step (b) of Example I.

(c) Quaternisation of p-dimethylainino benzamidopropyldimethylamine with poly(N-isopropyl acrylamide-c-vinyl benzyl chloride):

A mixture of copolymer of N-isopropyl acrylamide and vinyl benzyl chloride (2.0 g, 3.31 mol of vinyl benzyl chloride from the previous step (b), p-dimethylamino benzamidopropyldimethylamine (0.825 g, 3.31 mmol) in isopropanol (25 ml) was stirred under nitrogen at 80° C. for 48 hours. The progress of reaction was followed by estimation of chloride ions. After quantitative liberation of chloride ions (0.40%), the solvent from the reaction mass was removed using a rotary evaporator to give pale yellow coloured powdery solid. This powder was further used for recording IR and NMR. It was redissolved in water or propylene glycol to form 10% solution. $E^{1\%}_{1cm}$ of this quaternised copolymer was found to be 260 at λmax 298 nm.

Example IV

Preparation of Shampoo

A shampoo was formulated using polymer prepared in Example I. The other active ingredients, SLES-2, sodium lauryl ether sulphate, an anionic surfactant, 30% aqueous solution, CAPB, cocoamidopropyl betaine, an amphoteric surfactant, 30% aqueous solution, LAO, lauryl amine oxide, CMEA, cocomonoethanolamide and EGMS, ethylene glycol monostearate were obtained from Galaxy Surfactants Ltd., Mumbai, India. Methyl paraben and propyl paraben were obtained from Gayatri Laboratories, Mumbai, India. Approved fragrances and colors were obtained from S.H. Kelkar & Co., Mumbai, India and Koel Colors Pvt. Ltd., Mumbai, India respectively.

Composition of Shampoo

| Ingredients | % w/w |
|---|---|
| Sodium lauryl ether sulphate - 2 EO, SLES-2 | 50.0 |
| Cocoamidopropyl betaine, CAPB. | 2.5 |
| Lauryl amine oxide - LAO | 2.0 |
| Cocomonoethanolamide - CMEA | 2.0 |
| Ethylene glycol monostearate | 1.5 |
| Polymer of Example I | 1.0 |
| Disodium EDTA | 0.1 |
| NaCl | q.s |
| Fragrance | q.s |
| Colour | q.s |
| Formaldehyde | 0.05 |
| Parabens | 0.1 |
| Water | q.s to 100% |

The shampoo was prepared as follows:

To stirred SLES-2 (100.0 g), CAPB (5.0 g), LAO (4.0 g), CMEA (4.0), EGMS (3.0 g) and water (60.0 ml) were added and the temperature of the reaction mass was raised to 50° C. To this a solution of polymer of Example I (2.0 g) in water (20.0 ml) was added and stirring was continued till a homogeneous mixture was obtained. The resulting mixture was then cooled with continuous stirring. The required chelating agent, colour, perfume were added. The viscosity was adjusted to 2500 cps with addition of sodium chloride. The total weight of shampoo was adjusted to 200.0 g with water.

This shampoo formulation was evaluated for deposition of the polymer on hair (substantivity) and results are described in Example X.

Example V

Preparation of Transparent Bathing Bar

A transparent bathing bar was formulated using cationic polymer prepared as in Example I and other ingredients are given below.

Composition of Transparent Bathing Bar

| Ingredients | % w/w |
|---|---|
| SLES-2, Sodium lauryl ether sulphate, 2 E.O. | 28.0 |
| CAPB, Cocoamidopropyl betaine. | 16.0 |
| Propylene glycol | 20.0 |
| Sorbitol | 8.0 |
| Sodium cocoate | 9.0 |
| Sodium stearate | 13.8 |
| Polymer of Example I | 1.0 |
| Disodium EDTA | 0.1 |
| Fragrance | q.s |
| Colour | q.s |
| Water | q.s to 100% |

The transparent bathing bar was prepared as follows:

To a stirred mixture of SLES-2 (56.0 g) and CAPB (32.0 g), propylene glycol (40.0 g), sorbitol (16.0 g), a solution of polymer of Example I (2.0 g) in water (8 ml) was added and the mixture was heated to 70° C. To this mixture sodium cocoate (18.0 g) and sodium stearate (27.6 g) were added and the stirring was continued till the reaction mass became homogeneous and transparent. The reaction mass was cooled to 40° C. and the required amounts of disodium EDTA, perfume and colour were added. The molten mass was cast in moulds of desired shape to yield transparent bathing bar. It could be easily seen that the transparency of bathing bar was unaffected as was judged by simultaneous preparation of a transparent bathing bar without the cationic polymer.

The transparent bathing bar thus made was evaluated for deposition of the polymer through substantivity as described in Example XI.

Example VI

Preparation of Sunscreen Cream

A sunscreen cream was formulated using cationic polymer prepared as in Example I. Carbopol—ETD-2020 was obtained from B. F. Goodrich. Parsol-1789 was purchased from Givaudan.

Lauryl alcohol ethoxylate, ethylene glycol monostearate, glyceryl monostearate were obtained from Galaxy Surfactants Ltd., Mumbai, India.

Composition of Sunscreen Cream

| Ingredient | % w/w |
|---|---|
| Carbopol, ETD-2020 | 0.25 |
| Sodium lauryl sulphate | 2.0 |
| Polymer of Example I | 1.0 |
| Lauryl alcohol ethoxylate - 9 EO | 0.5 |
| Liquid paraffin oil | 4.0 |
| Isopropyl myristate | 5.0 |
| Cetostearyl alcohol | 5.0 |
| Glyceryl monostearate | 5.0 |
| Parsol-1789 | 1.0 |
| PEG-7-glyceryl cocoate | 1.5 |
| Glycerine | 2.0 |
| Propylene glycol | 4.0 |
| Sodium hydroxide | to adjust pH 6.0 to 6.5 |
| Preservatives, fragrance and chelating agents | q.s |
| Water | q.s to 100% |

The sunscreen cream was prepared as follows:

Carbopol, ETD-2020 (0.5 g) was dispersed in water (140 ml) at 70° C. To it glycerine (4.0 g), sodium lauryl sulphate (4.0 g) and preservatives were added. Oily phase containing isopropyl myristate (10.0 g), glyceryl monostearate (10.0 g), Parsol-1789 (2.0 g), paraffin oil (8.0 g), cetostearyl alcohol (10.0 g), lauryl alcohol ethoxylate-9 EO (1.0 g), PEG-7-glyceryl cocoate (4.0 g) were stirred at 70° C. The preheated oily phase was then added to the aqueous phase at 70° C. under vigorous stirring. To this mass a solution of polymer of Example I (2.0 g) in propylene glycol (8 ml) was added under stirring. Sodium hydroxide (10% solution) was added to adjust the pH between 6.0 to 6.5. Fragrance and chelating agents were added and cooled under stirring to room temperature to get a good, shiny cream.

A short exposure (30 minutes) to sunlight of a forearm with this cream applied on showed less darkening than the other forearm. Melanin content (measured using Mexameter-18) for untreated forearm was found to be 380 and for treated with sunscreen forearm was found to be 415.

Example VII

Preparation of Sunscreen Gel

A sunscreen gel was formulated using polymer prepared as in Example I. Carbopol—Ultrez-10 was obtained from B. F. Goodrich Composition of Sunscreen Gel

| Ingredient | % w/w |
|---|---|
| Carbopol - Ultrez-10 | 1.0 |
| Triethanolamine | to adjust pH |
| Polymer of Example I | 0.5 |
| Propylene glycol | 50 |
| Colour, perfume, chelating agents and preservatives | q.s |
| Water | q.s to 100% |

The sunscreen gel was prepared as follows:

Polymer of Example I (1.0 g) was added to propylene glycol (100 ml) and stirred for 5 minutes at 70° C. To this solution Carbopol—Ultrez-10 (2.0 g) in water (100 ml) was added slowly under stirring at 70° C. After all the Carbopol—Ultrez-10 was hydrated, it was then neutralised with triethanolamine (2.2 g) to pH 6.0 to 7.0 and stirring was continued to get a clear gel. Colour, perfume, chelating agents and preservatives were then added to this the gel.

Example VIII

Preparation of Sunscreen Spray

A sunscreen for hair and skin was formulated using polymer prepared as in Example I. Dimethicone copolyol SF-1288 was obtained from General Electric.

Composition of Sunscreen Spray

| Ingredient | % w/w |
|---|---|
| Dimethicone copolyol, SF 1288 | 2.0 |
| Polymer of Example I | 8.0 |
| Water | 10.0 |
| Perfume | q.s |
| Ethyl alcohol | q.s to 100% |

The sunscreen spray was prepared as follows:

Polymer of Example A (16.0 g), dimethicone copolyol (4.0 g), water (20.0 g) and ethyl alcohol (80.0 g) were mixed at room temperature to get a clear solution. To this solution, perfume was added and stirred.

Example IX

Preparation of Detergent Powder

A detergent powder was formulated using polymer prepared as in Example I. Linear alkyl benzene sulphonic acid was obtained from Albright and Wilson Chemicals (India) Ltd., Mumbai, India.

Composition of Detergent Powder

| Ingredient | % w/w |
|---|---|
| Soda ash | 20.0 |
| Sodium tripolyphosphate | 25.0 |
| Sodium chloride | 5.0 |
| Sodium sulphate | 20.0 |
| Sodium linear alkyl benzene sulphonate | 20.0 |
| Sodium carboxy methyl cellulose | 1.0 |
| Sodium silicate | 2.0 |
| Polymer of Example 1 | 2.0 |
| Lauryl alcohol ethoxylate | 1.0 |
| Bleaching agent | q.s |
| Optical brightener | q.s |
| Disodium EDTA | 1.0 |
| Colour | q.s |
| Fragrance | q.s |
| Water | q.s to 100% |

The detergent powder was prepared as follows:

Soda ash (40.0 g), sodium tripolyphosphate (50.0 g), sodium chloride (10.0 g) and sodium sulphate (40.0 g) were mixed well and sodium linear alkyl benzene sulphonate (40.0 g) was added to this mixture slowly while being stirred. This mixture was then cooled. Polymer of Example I (4.0 g), sodium carboxy methyl cellulose (2.0 g), sodium silicate (4.0 g) were then added to this mixture along with the other additives like lauryl alcohol ethoxylate (2.0 g), bleaching agent (sodium perborate), stilbene based optical brightener, disodium EDTA, colour and perfume. Water was added to the mixture if necessary to adjust the weight to 200.0 g and stirring was continued to get uniform detergent powder.

The detergent powder thus made was evaluated for the deposition of cationic polymer on cotton fabric (substantivity) and the results are described in Example XII.

Example X

Measurement of Substanitivity in Shampoo

Hair tresses (5.0 g) were washed with 10% SLES solution and rinsed with plain water. The tresses were treated with shampoo (containing 1.0% Polymer of Example I) as described in Example IV. After the treatment the tresses were washed thoroughly with copious amount of water. The adsorbed quaternary was extracted from the hair surface by immersing each tress in isopropanol at 65° C. for 30 minutes and the isopropanol extract was analysed spectrophotometrically.

The substantivity was found to be 53 mg/100 g of hair.

Example XI

Measurement of Substantivity in Transparent Bathing Bar

A soap (containing 1.0% Polymer of Example I) as described in Example V was applied on the inside of forearm (hairless or shaven) on a specified area. It was then washed off gently by holding forearm under tap water. The deposited sunscreen polymer was re-extracted with cotton swabs soaked in absolute ethanol. The volume of alcohol extract was made up and the absorbance was measured on UV spectrophotometer.

The substantivity was found to be 25 μg/cm$^2$ of skin.

Example XII

Measurement of Substantivity in Detergent Powder

A piece of cotton fabric (5.0 g) was washed with detergent solution and rinsed with water. It was then treated with detergent powder (5.0 g) of Example IX in water (200 ml) for 15 minutes. The cotton fabric was then removed and washed thoroughly with water. The adsorbed polymer was then extracted from the cotton fibres by immersing in isopropanol at 65° C. for 30 minutes. A known volume of this isopropanol/Polymer of Example I was analysed by UV spectroscopy to determine its absorption.

The substantivity on cotton fabric was found to be 43 mg/100 g of cotton fabric.

Advantages of the Process of the Present Invention:

The present invention gives salt and heat sensitive, UV-absorbing, water-soluble, cationic polymers containing cinnamidoalkylamines and/or benzamidoalkylamines. These polymers are substantive to hair, skin and fabric and hence are useful in personal care compositions and fabric care products.

The process of synthesising cationic polymer described in this invention allows appropriate selection of substituted monomers and their ratio to make the macromolecules not only hydrophilic but also with the property of 'inverse temperature dependant solubility'. This property makes these UV-absorbing polymers quite soluble at ambient temperature but they lose their solubility with increase in the temperature. Although, highly soluble in plain water at ambient temperature, they readily phase-separate from their aqueous solutions in the presence of electrolytes like common salt or sea water. Hence, the thin coat of these polymers that is applied to hair and skin through the cosmetic preparations does not get washed off by sea water during activity like swimming. In short, these macromolecules of the present invention are more substantive due to their inverse temperature dependent solubility behaviour. Thus, the excellent substantivity of the macromolecules of the present invention is the result of (a) polymeric nature, (b) the cationic centres as well as (c) reduced solubility of the polymers at temperatures equivalent to body temperature and in the presence of salt in water. The macromolecules of the present invention are soluble in both water and alcohol and thus hydrophobic phases that give greasy feel can be conveniently avoided while creating cosmetic compositions. Thus, the polymers of the present invention are useful for 'leave-on' as well as 'rinse-off' formulations. Their thermosensitivity and sensitivity towards salt offer unique advantage to formulate non-greasy beach products to protect from ravaging solar radiation.

We claim

1. Cationic, water-soluble polymers of Formula I, wherein;

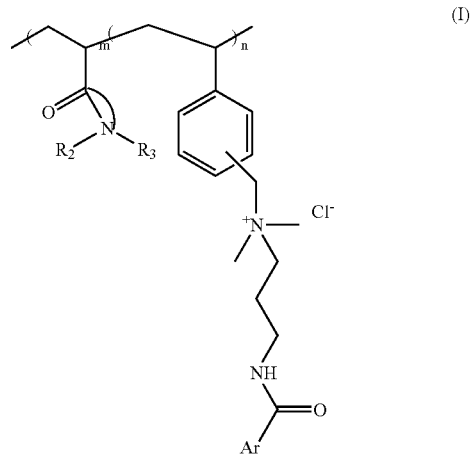

(I)

ArCO is an UV-absorbing moiety of an organic sunscreen acid or mixtures of organic sunscreen acids selected from p-methoxy cinnamic acid and p-dimethyl amino benzoic acid;

$R_2$ and $R_3$ are selected from hydrogen, alkyl and cycloalkyl group containing from 1 to 6 carbon atoms;

m is an integer from 5 to 9 and n is an integer between 1 to 5 and m+n=10.

2. A water-soluble polymer of claim 1, wherein ArCO=p-methoxy cinnamoyl, $R_2$=—H, $R_3$=isopropyl, m=8 and n=2.

* * * * *

UNITED STATES PATENT AND TRADEMARK OFFICE
CERTIFICATE OF CORRECTION

| | | |
|---|---|---|
| PATENT NO. | : 7,087,692 B2 | Page 1 of 1 |
| APPLICATION NO. | : 10/305087 | |
| DATED | : August 8, 2006 | |
| INVENTOR(S) | : Nirmal M. Koshti et al. | |

It is certified that error appears in the above-identified patent and that said Letters Patent is hereby corrected as shown below:

<u>Title Page:</u>
Item (75) Inventors, please change the name of the first inventor, "Nimul Madhukar Koshti" to --Nirmal Madhukar Koshti --.

Signed and Sealed this

Twenty-first Day of November, 2006

JON W. DUDAS
*Director of the United States Patent and Trademark Office*